(12) United States Patent
Chen et al.

(10) Patent No.: US 12,059,495 B2
(45) Date of Patent: Aug. 13, 2024

(54) USE OF A PLATELET DRY POWDER FOR RELIEVING INFLAMMATION OR INJURY IN A PORTION OF RESPIRATORY TRACT (OR THE AIRWAY)

(71) Applicants: Spirit Scientific Co. LTD., New Taipei (TW); Dao Lung Steven Lin, New Taipei (TW)

(72) Inventors: Chin-Ho Chen, New Taipei (TW); Yi-Shin Tsai, New Taipei (TW); Tzu-Min Yang, New Taipei (TW); Dao Lung Steven Lin, New Taipei (TW)

(73) Assignees: SPIRIT SCIENTIFIC CO. LTD., New Taipei (TW); Dao Lung Steven Lin, New Taipei (TW)

( * ) Notice: Subject to any disclaimer, the term of this patent is extended or adjusted under 35 U.S.C. 154(b) by 0 days.

(21) Appl. No.: 17/841,941

(22) Filed: Jun. 16, 2022

(65) Prior Publication Data

US 2022/0401359 A1 Dec. 22, 2022

Related U.S. Application Data

(60) Provisional application No. 63/212,250, filed on Jun. 18, 2021.

(51) Int. Cl.
| | |
|---|---|
| *A61K 9/00* | (2006.01) |
| *A61K 35/19* | (2015.01) |
| *A61K 38/18* | (2006.01) |
| *A61P 11/00* | (2006.01) |

(52) U.S. Cl.
CPC ............ *A61K 9/0078* (2013.01); *A61K 35/19* (2013.01); *A61K 38/1808* (2013.01); *A61K 38/1825* (2013.01); *A61K 38/1858* (2013.01); *A61K 38/1866* (2013.01); *A61P 11/00* (2018.01)

(58) Field of Classification Search
CPC .............. A61K 9/0078; A61K 38/1858; A61K 38/1825; A61K 38/1808; A61K 35/19; A61P 11/00

See application file for complete search history.

(56) References Cited

U.S. PATENT DOCUMENTS

| | | | |
|---|---|---|---|
| 9,878,011 B2 * | 1/2018 | Landrigan | A61K 35/14 |
| 10,993,965 B2 * | 5/2021 | Patel | A61K 8/893 |
| 2013/0061849 A1 | 3/2013 | Lemper | |
| 2013/0195959 A1 | 8/2013 | Patel | |

FOREIGN PATENT DOCUMENTS

| | | |
|---|---|---|
| TW | I480066 B | 4/2015 |
| WO | WO 2013/113024 A1 | 8/2013 |

OTHER PUBLICATIONS

Beitia M, Delgado D, Sanchez P, Vallejo de la Cueva A, Cugat JR, Sanchez M. Int J Mol Sci. Feb. 12, 20212; 22(4): 1856. (Year: 2021).*

Beitia et al."Platelet Lysate Nebulization Protocol for the Treatment of COVID-19 and Its Sequels: Proof of Concept and Scientific Rationale" International Journal of Molecular Sciences, vol. 22, No. 1856, Feb. 12, 2021, pp. 1-18.

Kieb et al., "Platelet-Rich Plasma Poweder; A New Preparation Method for the Standardization of Growth Factor Concentrations" The American Journal of Sports Medicine, vol. 45, No. 4, 2016, pp. 954-960.

Queiroz Da Silva et al., "Platelet-rich plasma lyophilization enables growth factor preservation and functionality when compared with fresh platelet-rich plasma," Regenerative Medicine, vol. 13, No. 7, 2018, pp. 775-784.

* cited by examiner

*Primary Examiner* — Valarie E Bertoglio
*Assistant Examiner* — Zanna Maria Beharry
(74) *Attorney, Agent, or Firm* — WPAT, PC

(57) ABSTRACT

The present invention provides a use of platelet dry powder (PDP) for relieving inflammation or injury in an airway portion, wherein per gram of platelet dry powder (PDP) comprises at least 100,000 platelets.

19 Claims, 11 Drawing Sheets

Fig. 1

| Illustration of lungs | Aperture size range (μm) | NGI location |
|---|---|---|
| | 8.61~14.10 μm | Stage 1 |
| | 5.39~8.61 μm | Stage 2 |
| | 3.3~5.39 μm | Stage 3 |
| | 2.08~3.30 μm | Stage 4 |
| | 1.36~2.08 μm | Stage 5 |
| | 0.98~1.36 μm | Stage 6 |
| | <0.98 μm | Stage 7 |

Fig 6

USE OF A PLATELET DRY POWDER FOR RELIEVING INFLAMMATION OR INJURY IN A PORTION OF RESPIRATORY TRACT (OR THE AIRWAY)

CROSS REFERENCE TO RELATED APPLICATION

This non-provisional application claims the benefit under 35 U.S.C. § 119(e) to U.S. Provisional Application No. 63/212,250, filed on Jun. 18, 2021, all of which are hereby expressly incorporated by reference into the present application.

FIELD OF THE INVENTION

The present invention relates to a Platelet dry powder (PDP); more particularly relates to a Platelet dry powder (PDP) that is used for relieving inflammation or injury to a portion of respiratory tract (or the airway).

BACKGROUND OF THE INVENTION

Inflammation is the body's defense mechanism Inflammation in body parts is often triggered by infection, trauma or hypersensitivity reactions to eliminate harmful irritants and pathogens and to promote tissue repair. Inflammation is divided into acute inflammation and chronic inflammation such as allergic rhinitis, pneumonia, hepatitis, and enteritis. Severe pneumonia can even lead to diseases such as chronic obstructive pulmonary disease (COPD) and pulmonary fibrosis; while severe hepatitis can lead to diseases such as liver cirrhosis and cancer.

The human respiratory tract consists of the nasal cavity, nasal mucosa, trachea, bronchi, bronchioles, respiratory bronchioles, alveolar ducts, and alveoli. When various portions of the respiratory tract are infected, exposed to toxins or exposed to pollutants, the body will initiate an inflammatory response, which in turn leads to respiratory inflammation-related diseases such as bronchitis, bronchiectasis, occlusive bronchitis, pneumonia, pleurisy, pulmonary fibrosis, emphysema, idiopathic pulmonary fibrosis (IFP), and chronic obstructive pulmonary disease (COPD). Among them, Coronavirus Disease-2019 (COVID-19) started spreading worldwide in late 2019. This pneumonia is caused by subjects infected with Severe Acute Respiratory Syndrome Coronavirus 2 (SARS-CoV-2) and can cause severe pneumonia, respiratory distress syndrome or multi-organ failure, shock, and even death in severe cases. Since the end of 2019, Coronavirus Disease-2019 has become a global pandemic and has been declared a public health emergency of international concern (PHEIC) by the World Health Organization (WHO) on Jan. 30, 2020.

Platelet-rich plasma (PRP) is a blood-derived product with a platelet concentration of approximately 1.5 to 5 times that of normal blood. Platelet contains platelet-related growth factors such as Platelet-Derived Growth Factor (PDGF), Vascular Endothelial Growth Factor (VEGF), Epidermal Growth Factor (EGF), Fibroblast Growth Factor (FGF), and Transforming Growth Factor Beta 1 (TGF-β1).

Platelet-rich plasma (PRP) has anti-inflammatory properties (Reference 1). However, clinical studies have found that the inability of Platelet-rich plasma (PRP) to effectively suppress inflammation is due to die lack of standardized preparation methods for Platelet-rich plasma (PRP), resulting in its inconsistent quality. In addition, the clinical application of platelet-rich plasma (PRP) during nebulization, especially in relieving inflammation and injury in various portions of the respiratory tract, lacks testing and data support, such as recovery, nebulization time, and effective concentration, Therefore, it is difficult to be applied in clinical treatment.

There is a pressing need in the market for a pharmaceutical composition that can break through the limitations of the prior art to relieve or treat inflammation or injury in various portions of the respiratory tract.

SUMMARY OF THE INVENTION

In view of the shortcomings of the prior art, it is an object of the present invention to provide a platelet dry powder that is effective in relieving (or alleviating) or treating inflammation or injury of the respiratory tract.

The second objective of the present invention is to provide a platelet dry powder, which is prepared by a standardized process and has a consistent quality (i.e. the same number of platelets in each batch).

The third objective of the present invention is to improve the recovery of growth factors after nebulization.

The fourth object of the present invention is to reduce the time required for nebulization.

The present invention provides the use of a platelet dry powder in the manufacture of aerosols for relieving the degree of inflammation or injury in the respiratory tract portion (or airway portion) of a subject by administering an effective amount of the aerosols to the respiratory tract portion (or airway portion) of the subject; wherein the number of platelets per gram (g) of the platelet dry powder is $1 \times 10^6 \sim 1 \times 10^{12}$ (1,000,000~1,000,000,000,000).

Preferably, the number of platelets per gram (g) of Platelet dry powder is $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$ (2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, 100,000,000, 200,000,000, 300,000,000, 400,000,000, 500,000,000, 600,000,000, 700,000,000, 800,000,000, 900,000,000, 1,000,000,000, 2,000,000,000, 3,000,000,000, 4,000,000,000, 5,000,000,000, 6,000,000,000, 7,000,000,000, 8,000,000,000, 9,000,000,000, 10,000,000,000, 20,000,000,000, 30,000,000,000, 40,000,000,000, 50,000,000,000, 60,000,000,000, 70,000,000,000, 80,000,000,000, 90,000,000,000, 100,000,000,000, 200,000,000,000, 300,000,000,000, 400,000,000,000, 500,000,000,000, 600,000,000,000, 700,000,000,000, 800,000,000,000, 900,000,000,000).

Preferably, the step of preparing the aerosols comprises: a. mixing the Platelet dry powder with a solvent to obtain a Platelet dry powder solution/suspension (PDPS); and b. using an aerosol generator to nebulize the platelet dry powder solution/suspension (PDPS) to obtain a plurality of aerosols.

Preferably, the aerosols enter the subject through the mouth or nose of the subject, thereby reaching the respiratory tract portion.

Preferably, the number of platelets per gram (g) of Platelet dry powder is $5 \times 10^9 \sim 1 \times 10^{11}$ (5,000,000,000~100,000,000,000).

Preferably, the number of platelets per gram (g) of Platelet dry powder is $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ (6,000,000,000, 7,000,000,000, 8,000,000,000, 9,000,000,000, 10,000,000,000, 20,000,000,000, 30,000,000,000, 40,000,000,000, 50,000,000,000, 60,000,000,000, 70,000,000,000, 80,000,000,000, or 90,000,000,000).

Preferably, the content of PDGF-BB per gram (g) of the Platelet dry powder is 0.01~20,000 ng.

Preferably, the content of PDGF-BB per gram (g) of the Platelet dry powder is 0.5, 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1,000, 1,250, 1,500, 1,750, 2,000, 2,250, 2,500, 2,750, 3,000, 3,250, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000, 8,250, 8,500, 8,750, 9,000, 9,250, 9,500, 9,750, 10,000, 11,000, 12,000, 13,000, 14,000, 15,000, 16,000, 17,000, 18,000, or 19,000 ng.

Preferably, the content of PDGF-BB per gram (g) of the Platelet dry powder is 50~1,500 ng.

Preferably, the content of PDGF-BB per gram (g) of the Platelet dry powder is 90~1,200 ng.

Preferably, the content of PDGF-BB per gram (g) of the Platelet dry powder is 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, or 1,450 ng.

Preferably, the content of VEGF per gram (g) of the Platelet dry powder is 200~200,000 pg.

Preferably, the content of VEGF per gram (g) of the Platelet dry powder is 5,000~80,000 pg.

Preferably, the content of VEGF per gram (g) of the Platelet dry powder is 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,500, 4,000, 4,500, 5,000, 5,500, 6,000, 6,500, 7,000, 7,500, 8,000, 8,500, 9,000, 10,000, 15,000, 20,000, 25,000, 30,000, 35,000, 40,000, 45,000, 50,000, 55,000, 60,000, 65,000, 70,000, 75,000, 79,000, 80,000, 85,000, 90,000, 95,000, 100,000, 105,000, 110,000, 115,000, 120,000, 125,000, 130,000, 135,000, 140,000, 145,000, 150,000, 155,000, 160,000, 165,000, 170,000, 175,000, 180,000, 185,000, 190,000, 195,000, or 199,000 pg.

Preferably, the content of FGF per gram (g) of the Platelet dry powder is 10~7,000 pg.

Preferably, the content of FGF per gram (g) of the Platelet dry powder is 100~3,000 pg.

Preferably, the content of FGF per gram (g) of the Platelet dry powder is 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,500, 3,000, 3,500, 4,000, 4,500, 5,000, 5,500, 6,000, 6,200, 6,400, 6,600, 6,800, or 6,900 pg.

Preferably, the content of TGF-β1 per gram (g) of the Platelet dry powder is 200~10,000 ng.

Preferably, the content of TGF-β1 per gram (g) of the Platelet dry powder is 250~7,000 ng.

Preferably, the content of TGF-β1 per gram (g) of the Platelet dry powder is 210, 220, 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,500, 3,000, 3,500, 4,000, 4,500, 5,000, 5,500, 6,000, 6,200, 6,400, 6,600, 6,800, or 6,900 ng.

Preferably, the content of EGF per gram (g) of the Platelet dry powder is 0.5~500 ng.

Preferably, the content of EGF per gram (g) of the Platelet dry powder is 10~210 ng.

Preferably, the content of EGF per gram (g) of the Platelet dry powder is 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 495 ng.

Preferably, the content of albumin per gram (g) of the Platelet dry powder is 0~3 g.

Preferably, the content of albumin per gram (g) of the Platelet dry powder is 0.25, 0.5, 0.75, 1, 1.25, 1.5, 1.75, 2, 2.25, 2.5, or 2.75 g.

Preferably, the content of albumin per gram (g) of the Platelet dry powder is 0~1 g.

Preferably, the content of albumin per gram (g) of the Platelet dry powder is 0.25, 0.5, or 0.75 g.

Preferably, the content of globulin per gram (g) of the Platelet dry powder is 0~2 g.

Preferably, the content of globulin per gram (g) of the Platelet dry powder is 0.25, 0.5, 0.75, 1, 1.25, 1.5, or 1.75 g.

Preferably, the content of globulin per gram (g) of the Platelet dry powder is 0~1 g.

Preferably, the content of globulin per gram (g) of the Platelet dry powder is 0.25, 0.5, or 0.75 g.

Preferably, the solvent is sterile normal saline, water for injection, 0.45% NaCl, 4.5% hypertonic saline, sterile thermal water, or isotonic saline.

Preferably, the number of white blood cells (WBC) per gram (g) of the Platelet dry powder is $0\sim9\times10^5$ (0~900,000).

Preferably, the number of white blood cells (WBC) per gram (g) of the Platelet dry powder is 50, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, or 800,000.

Preferably, the number of white blood cells (WBC) per gram (g) of the Platelet dry powder is 0~3,000.

Preferably, the number of white blood cells (WBC) per gram (g) of the Platelet dry powder is 0~2,000.

Preferably, the number of platelets per milliliter (mL) of the Platelet dry powder solution/suspension (PDPS) is $1\times10^8\sim1\times10^{11}$ (100,000,000~100,000,000,000).

Preferably, the number of platelets per milliliter (mL) of the Platelet dry powder solution/suspension (PDPS) is $1\times10^9\sim1\times10^{10}$ (1,000,000,000~10,000,000,000).

Preferably, the number of platelets per milliliter (mL) of the Platelet dry powder solution/suspension (PDPS) is $2\times10^9$, $3\times10^9$, $4\times10^9$, $5\times10^9$, $6\times10^9$, $7\times10^9$, $8\times10^9$, or $9\times10^9$ (2,000,000,000, 3,000,000,000, 4,000,000,000, 5,000,000,000, 6,000,000,000, 7,000,000,000, 8,000,000,000, or 9,000,000,000).

Preferably, the number of white blood cells (WBC) per milliliter (mL) of the Platelet dry powder solution/suspension (PDPS) is 0~1×10⁶ (0~1,000,000).

Preferably, the number of white blood cells (WBC) per milliliter (mL) of the Platelet dry powder solution/suspension (PDPS) is 1×10⁵~1×10⁶ (100,000~1,000,000).

Preferably, the number of white blood cells (WBC) per milliliter (mL) of the Platelet dry powder solution/suspension (PDPS) is 50, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, or 1,000,000.

Preferably, the concentration of PDGF-BB in the Platelet dry powder solution/suspension (PDPS) is 0.03~25 ng/mL.

Preferably, the concentration of PDGF-BB in the Platelet dry powder solution/suspension (PDPS) is 0.05, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, or 25 ng/mL.

Preferably, the concentration of PDGF-BB in the Platelet dry powder solution/suspension (PDPS) is 0.25~12 ng/mL.

Preferably, the concentration of VEGF in the Platelet dry powder solution/suspension (PDPS) is 10~4,000 pg/mL.

Preferably, the concentration of VEGF in the Platelet dry powder solution/suspension (PDPS) is 60~1,000 pg/mL.

Preferably, the concentration of VEGF in the Platelet dry powder solution/suspension (PDPS) is 11, 12, 13, 14, 15, 16, 17, 18, 19, 20, 21, 22, 23, 24, 25, 26, 27, 28, 29, 30, 33, 35, 37, 39, 40, 43, 45, 47, 49, 50, 53, 55, 57, 59, 60, 65, 70, 75, 80, 85, 90, 95, 100, 110, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,500, 3,000, 3,300, 3,500, 3,700, or 3,900 pg/mL.

Preferably, the concentration of FGF in the Platelet dry powder solution/suspension (PDPS) is 1~200 pg/mL.

Preferably, the concentration of FGF in the Platelet dry powder solution/suspension (PDPS) is 15~50 pg/mL.

Preferably, the concentration of FGF in the Platelet dry powder solution/suspension (PDPS) is 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 35, 40, 45, 50, 55, 60, 65, 70, 75, 80, 85, 90, 95, 100, 110, 120, 130, 140, 150, 160, 170, 180, 190, or 195 pg/mL.

Preferably, the concentration of TGF-β1 in the Platelet dry powder solution/suspension (PDPS) is 5~250 ng/mL.

Preferably, the concentration of TGF-β1 in the Platelet dry powder solution/suspension (PDPS) is 40~100 ng/mL.

Preferably, the concentration of TGF-β1 in the Platelet dry powder solution/suspension (PDPS) is 5.1, 5.2, 5.3, 5.4, 5.5, 5.6, 5.7, 5.8, 5.9, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 35, 40, 45, 50, 55, 60, 65, 70, 75, 80, 85, 90, 95, 100, 110, 120, 130, 140, 150, 160, 170, 180, 190, 200, 210, 220, 230, 240, or 245 ng/mL.

Preferably, the concentration of EGF in the Platelet dry powder solution/suspension (PDPS) is 0.1~10 ng/mL.

Preferably, the concentration of EGF in the Platelet dry powder solution/suspension (PDPS) is 2~4 ng/mL.

Preferably, the concentration of EGF in the Platelet dry powder solution/suspension (PDPS) is 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, or 9.8 ng/mL.

Preferably, the concentration of albumin in the Platelet dry powder solution/suspension (PDPS) is 0~3 g/dL.

Preferably, the concentration of albumin in the Platelet dry powder solution/suspension (PDPS) is 0.25, 0.5, 0.75, 1, 1.25, 1.5, 1.75, 2, 2.25, 2.5, or 2.75 g/dL.

Preferably, the concentration of albumin in the Platelet dry powder solution/suspension (PDPS) is 0~1.5 g/dL.

Preferably, the concentration of albumin in the Platelet dry powder solution/suspension (PDPS) is 0.25, 0.5, 0.75, 1, or 1.25 g/dL.

Preferably, the concentration of globulin in the platelet dry powder solution/suspension (PDPS) is 0~2 g/dL.

Preferably, the concentration of globulin in the Platelet dry powder solution/suspension (PDPS) is 0.25, 0.5, 0.75, 1, 1.25, 1.5, or 1.75 g/dL.

Preferably, the concentration of globulin in the Platelet dry powder solution/suspension (PDPS) is 0~1.5 g/dL.

Preferably, the concentration of globulin in the Platelet dry powder solution/suspension (PDPS) is 0.25, 0.5, 0.75, 1, or 1.25 g/dL.

Preferably, the aerosol generator is a non-invasive ventilation (NIV), nebulizer, ultrasonic nebulizer, small volume nebulizer (SVN), jet nebulizer, mesh nebulizer, vibrating mesh nebulizer, soft mist inhaler, or adaptive aerosol delivery (AAD).

Preferably, the subject allows the aerosols to enter mouth or nose of the subject by maintaining spontaneous ventilation, mechanically air delivery, or pressure controlled ventilation, etc., to reach the respiratory tract (or airway).

Preferably, the aerosol generator can be attached to a mouthpiece or a mask to deliver the aerosols to the respiratory tract portion of the subject through the mouth or nose of the subject.

Preferably, the respiratory tract portion is the nasal cavity, nasal mucosa, trachea, bronchi, bronchioles, respiratory bronchioles, alveolar ducts, alveoli or lungs.

Preferably, the inflammation is bronchitis, bronchiectasis bronchiolitis, occlusive bronchitis, inflammation of the lung, or pleurisy.

Preferably, the injury is pulmonary fibrosis, emphysema, idiopathic pulmonary fibrosis (IFP), chronic obstructive pulmonary disease (COPD), bronchiectasis, sarcoidosis, inhalation injury, radiation injury, burn injury, injury caused by cancer, injury caused by pathogen invasion, physical injury, injury from Coronavirus Disease-2019 (COVID-19) infection, acute lung injury (ALI), acute respiratory distress syndrome (ARDS), or pulmonary contusion.

Preferably, the inflammation or injury is caused by at least one of the following etiological factors: upper respiratory tract infections, lower respiratory tract infections or pneumonia, coronavirus disease-2019 (COVID-19) infection, tobacco hazards, smog, and air pollution.

Preferably, the subject is a mammal

Preferably, the subject is a human.

Preferably, the Platelet dry powder is prepared from an autologous blood sample or an allogeneic blood sample.

Preferably, the aerosol generator has a chip to control an nebulization parameter, so that the output aerosols can achieve an nebulization effect.

Preferably, the nebulization parameters are the operating environment temperature of 10~40° C., relative humidity of 30~90%, and the nebulization effect is to output a total volume of 0.2~10 mL of aerosols per unit time (according to the recommendations of the nebulizer model used).

The present invention further provides a non-therapeutic method for alleviating the degree of inflammation in a portion of a subject respiratory tract comprising the steps of: a. mixing a Platelet dry powder with a solvent to obtain Platelet dry powder solution/suspension (PDPS); b. nebulizing the Platelet dry powder solution/suspension (PDPS) using an aerosol generator to obtain a plurality of aerosols, and c. delivering the aerosols through the mouth or nose of the subject delivery to the respiratory tract portion of the subject.

The present invention further provides a non-therapeutic method for alleviating the degree of inflammation in a portion of the a subject respiratory tract comprising the steps of: a. using an aerosol generator to nebulize the Platelet dry powder solution/suspension (PDPS) to obtain a plurality of aerosols, and b. delivering the aerosols to the subject respiratory tract portion through the mouth or nose of the subject.

Preferably, the number of white blood cells (WBC) per gram (g) of the Platelet dry powder is 0~3,000; or the number of white blood cells (WBC) per milliliter (mL) of the Platelet dry powder solution/suspension (PDPS) is $1\times10^5$~$1\times10^6$ (100,000~1,000,000).

Preferably, the number of platelet per gram (g) of the Platelet dry powder is $1\times10^8$~$1\times10^{12}$ (100,000,000~1,000,000,000,000); or the number of platelets per milliliter (mL) of the Platelet dry powder solution/suspension (PDPS) is $1\times10^8$~$1\times10^{11}$ (100,000,000~10,000,000,000).

Preferably, the number of platelet per gram (g) of the Platelet dry powder is $5\times10^9$~$1\times10^{11}$ (5,000,000,000~100,000,000,000); or the number of platelets per milliliter (mL) of the Platelet dry powder solution/suspension (PDPS) is $1\times10^9$~$1\times10^{10}$ (1,000,000,000~10,000,000,000).

Preferably, the content of PDGF-BB per gram (g) of the Platelet dry powder is 50~1,500 ng; and the concentration of PDGF-BB in the Platelet dry powder solution/suspension (PDPS) is 0.25~20 ng/mL.

Preferably, the content of PDGF-BB per gram (g) of the Platelet dry powder is 90~1,200 ng and the concentration of PDGF-BB in the Platelet dry powder solution/suspension (PDPS) is 0.25~12 ng/mL.

The present invention further provides use the Platelet dry powder in the manufacture of pharmaceutical aerosols for the treatment of respiratory tract (or airway) injuries with a platelet count of $1\times10^8$~$1\times10^{12}$ (100,000,000~1,000,000,000,000) per gram (g) of the Platelet dry powder.

BRIEF DESCRIPTION OF THE DRAWING

FIG. 1: The histogram shows the effect of PDGF-BB concentration in Platelet dry powder solution/suspension (PDPS) on the recovery of PDGF-BB after nebulization.

FIG. 6: The aperture size of each state of the Next Generation Impactor (NGI™) and respiratory tract (or the airway) site simulated by the stage.

DETAILED DESCRIPTION OF THE INVENTION

Figure 2A:
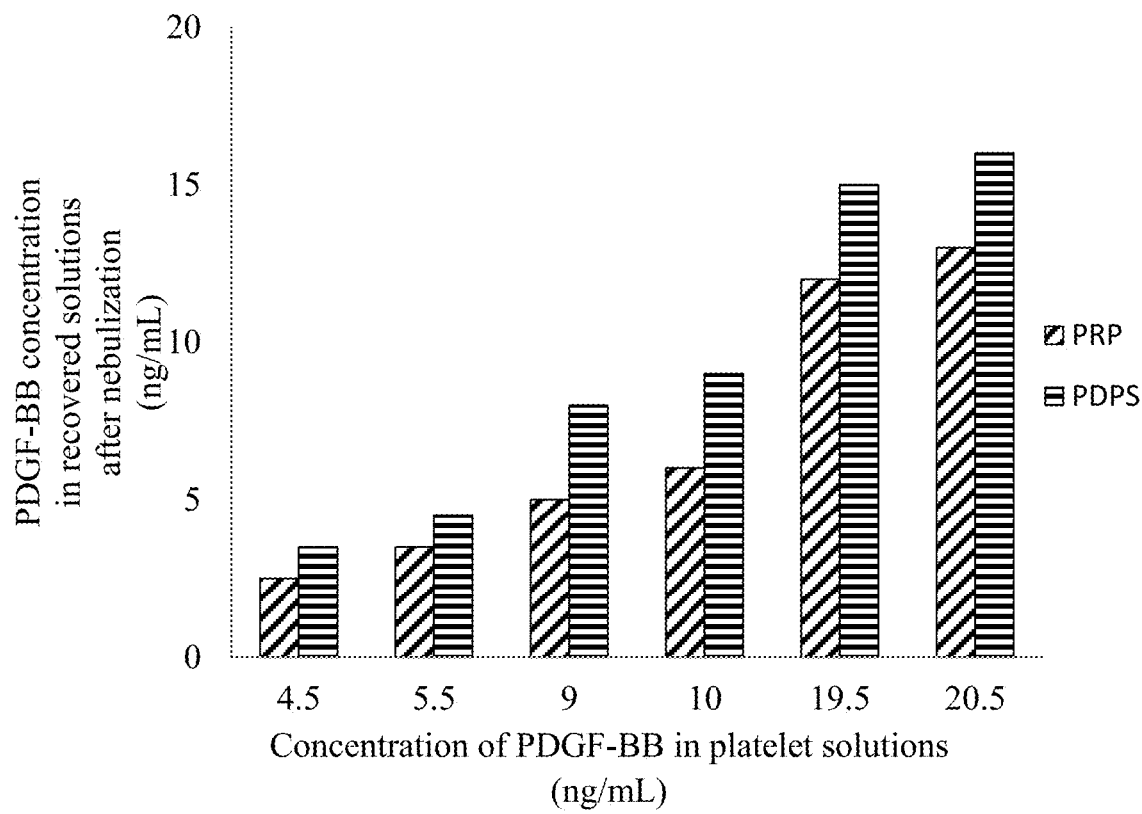
FIG. 2A: The histogram shows the effect of PDGF-BB concentration in different types of platelet solutions on the PDGF-BB concentration in the recovered solution after nebulization.

The following is a detailed description of the embodiments of the present invention, as well as the technology and features of the present invention. However, this embodiment is not intended to limit the present invention, and any changes and modifications made by anyone who is familiar with the technology without departing from the spirit and scope of the present invention should be included in the scope of the patent application of the present invention.

Embodiment 1: Prepare Platelet Dry Powder and Analyze the Composition Thereof

Embodiment 1-1: Preparation of Platelet Dry Powder

Human whole blood was put into a centrifuge tube containing anticoagulant, and centrifuged the human whole blood with a centrifuge (1500~2000 g, 10~15 minutes; this was the first centrifugation) to separate the human whole blood into three layers, from top to bottom were the plasma layer, the buffy coat layer, where white blood cells were located in this layer, and the red blood cell layer (see Reference 2~5). These steps and the stratification of blood cells after centrifugation are well known to those skilled in the art, and the centrifugation conditions of the first centrifugation can be expanded to 500~3,000 g for 5~20 minutes. After centrifugation, platelets were distributed in the plasma layer and adjacent to the buffy coat layer. Aseptically, aspirated the plasma layer and the buffy coat layer to obtain a mixture of the plasma layer and the buffy coat layer, which was Platelet-Rich Plasma (PRP).

Platelet-Rich Plasma (PRP) was centrifuged (700~1,200 g, 5 minutes) using a centrifuge. The centrifugation conditions can be expanded to 100~1,000 g, 5-10 minutes, and the force must be lower than the actual one used in the first centrifugation (500~3,000 g, 5~20 minutes), so that the PRP can be divided into upper and lower parts containing two-layer solution. The upper layer solution and the lower layer solution were aseptically separated to completely remove white blood cells (WBC) located in the lower layer solution. An Automatic Hemocytometer Analyzer (XP-300™ model, SYSMEX™ brand) was used to detect the number of platelets in the upper layer solution, and then the platelet concentration in the upper layer solution was adjusted to $1\times10^9$/mL. Reagents were added to avoid reductions in growth factor concentrations due to platelet breakage, apoptosis, or decreased activity. Reagents can be such as calcium chloride, thrombin, adenosine diphosphate. Centrifuged at 2,500~3,000 g for 10 minutes; the centrifugation conditions can be expanded to 500~4,000 g for 10~15 minutes, and the force must be higher than the actual one used in the first centrifugation (500~3,000 g, 5~20 minutes), so that the platelets can gather at the bottom. Completely removed the supernatant to completely remove the plasma and the protein in the plasma, then added the same volume of water for injection as the supernatant to obtain the solution to be dispensed.

During the above preparation steps, reagents can be left out (to avoid a decrease in growth factor concentration due to platelet rupture, apoptosis or reduced activity).

The solution to be dispensed was dispensed into sample bottles so that each sample bottle was filled with 1 milliliter (mL) of the solution to be dispensed, and then freeze-dried. The steps of freeze-drying are: (1) pre-cooling (−30~−50° C., at least 5 hours), (2) primary drying (temperature raised from step (1) to 10° C., 10~20 hours, vacuum value was less than or equal to 100 mTorr), (3) secondary drying (20° C., 3~5 hours, vacuum value less than or equal to 100 mTorr). After freeze-drying, the dried product is Platelet Dry Powder.

Preferably, each bottle of Platelet dry powder contains $1\times10^9$ platelets. The number of platelets in the Platelet dry powder can be detected by microscope counting or by a fully automated blood cell analyzer or other means.

As can be seen from the above preparation steps, Platelet-rich plasma (PRP) contains large amounts of white blood cells (WBC) and plasma in which the plasma contains large amounts of albumin and globulin, such as immunoglobulin G (IgG) platelet solution. The Platelet dry powder preparation step includes steps to remove white blood cells (WBC) and plasma, and includes a drying step (e.g., by freezing, low temperature or vacuum, etc.). Therefore, Platelet dry powder contained low concentration or even no white blood cells (WBC).

Preferably, platelet dry powder contains low concentration or even no albumin.

Preferably, Platelet dry powder contains low concentration or even no globulin.

Embodiment 1-2: Analysis of the Composition of Platelet Dry Powder

Using Analytical Balance (ME204 model, Mettler brand) to measure the weight of 5 bottles of Platelet dry powder. Mixed 5 bottles of Platelet dry powder with 1 mL of normal saline respectively to obtain 5 bottles of Platelet dry powder solution/suspension (PDPS). An Automated Hematology Analyzer (XP-300™ model, SYSMEX™ brand) was used to analyze the number of white blood cells (WBC) in each bottle of Platelet dry powder solution/suspension (PDPS), and used enzyme-linked immunosorbent assay (ELISA) to analyze the concentration of various growth factors (including PDGF-BB, VEGF, EGF, FGF, TGF-β1). The experimental results showed that the concentrations of PDGF-BB, VEGF, EGF, FGF, TGF-β1 in Platelet dry powder solution/suspension (PDPS) were 12.3~15.6 ng/mL, 733.4~943.6 pg/mL, 2.1~2.5 ng/mL, 19.2~31.9 pg/mL, and 49.7~85.1 ng/mL respectively, and the number of white blood cells (WBC) per microliter (μL) of Platelet dry powder solution/suspension (PDPS) was 0~100. Use the concentration of various growth factors and white blood cells (WBC) in Platelet dry powder solution/suspension (PDPS), and back-calculated the weight of various growth factors and the number of white blood cells (WBC) per gram (g) of Platelet dry powder. The experimental results are shown in Table 1:

TABLE 1

| Platelet dry powder Test items | mean ± standard deviation |
|---|---|
| Platelet dry powder net weight (g) | 0.06 ± 0.07 |
| Platelet count (×10$^{10}$/g) | 3.45 ± 3.26 |
| Number of white blood cells (WBC) (number/ng) | 0~100 |
| PDGF-BB content (ng) per gram (g) of Platelet dry powder | 440.6 ± 392.1 |
| VEGF content (pg) per gram (g) of Platelet dry powder | 27,188.6 ± 23,410.2 |
| EGF content (ng) per gram (g) of Platelet dry powder | 74.3 ± 67.5 |
| FGF content (ng) per gram (g) of Platelet dry powder | 959.4 ± 863.3 |
| TGF-β1 content (ng) per gram (g) of Platelet dry powder | 2,577 ± 2,385.3 |

As shown in Table 1, the average weight of each bottle of Platelet dry powder was 0.06 grams (g). The Platelet dry powder contained $3.45\times10^{10}$ platelets, 440.6 ng of PDGF-BB, 27,188.6 pg of VEGF, 74.3 ng of EGF, 959.4 pg of FGF, and 2,577 ng of TGF-β1 per gram (g) on average with no detectable leukocytes perng of platelet dry powder on average (or approximately 0-100 white blood cells (WBC)).

Embodiment 2: The Effect of Growth Factor Concentration of Platelet Dry Powder Solution/Suspension (PDPS) on the Recovery of PDGF-BB after Nebulization Among the various growth factors that are released from platelets, PDGF-BB plays the most important role in repairing damaged cells and promoting cell growth. Therefore, the inventors of the present invention conducted the following experiments to confirm whether PDGF-BB would be affected after being nebulized.

The platelet dry powder was mixed with normal saline to obtain Platelet dry powder solution/suspension (PDPS). The concentration of PDGF-BB in Platelet dry powder solution/ suspension (PDPS) was analyzed by enzyme-linked immunosorbent assay (ELISA). The concentration of growth factor PDGF-BB in the platelet dry powder solution/suspension (PDPS) was adjusted to 100 ng/mL with normal saline, and then serially diluted with water for injection to prepare 7 groups of platelet dry powder solutions/suspension (PDPS) dilution containing different concentrations of PDGF-BB. The PDGF-BB concentrations in the 7 groups of Platelet dry powder solution/suspension (PDPS) dilution were 1.1, 2.8, 5.2, 12, 22.4, 29.2, and 56.2 ng/mL, respectively.

3 mL of Platelet dry powder solution/suspension (PDPS) dilutions were taken from each group separately and nebulized with an aerosol generator (Pulmogine™ model, HCmed brand) to obtain multiple aerosols for each group of Platelet dry powder solution/suspension (PDPS) dilutions, respectively. The aerosol generator such as those that comply with the "Quality Management System for Medical Devices (QMS)" guidelines for medical devices, or those approved for marketing by the health authorities such as the FDA the medical Pulmogine™ nebulizer (HCmed), the medical NEB 800 nebulizer (Microlife®), or the medical TD-7001 nebulizer (Clever Check™). The aerosol generator used in this embodiment has a pore of 5 µm, and the aerosol generator is mainly composed of two parts, the upper part is the reservoir and the lower part is the main unit. The Platelet dry powder solution suspension (PDPS) dilutions is poured into the reservoir, the lid of the reservoir is closed, and the reservoir is connected to the lower part of the main unit; then the centrifuge tube is connected to the reservoir to collect the recovered solution after nebulization. Press the start button on the main unit to nebulize all the Platelet dry powder solution/suspension (PDPS) dilutions into aerosols. In this embodiment, the nebulized aerosols are collected in centrifuge tubes, and the aerosols collect in the centrifuge tube to form a recovered solution, which is further analyzed for the volume of the recovered solution and the concentration of PDGF-BB in the recovered solution by enzyme-linked immunosorbent assay (ELISA).

Figure 1:
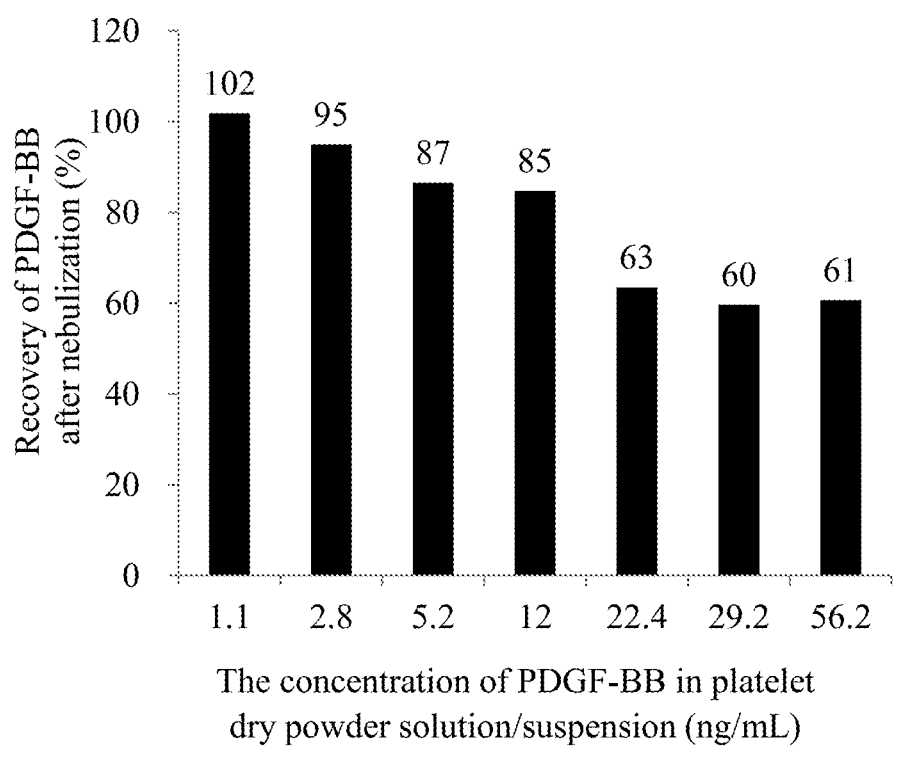

The Platelet dry powder solution/suspension (PDPS) dilutions of each group were nebulized separately, and the recovered volume and concentration of PDGF-BB after nebulization of the Platelet dry powder solution/suspension (PDPS) dilutions of each group were further analyzed, and the recovery of PDGF-BB after nebulization was calculated. The results of the experiments are shown in Table 2, Table 3, and FIG. 1.

TABLE 2

| Group | The concentration of PDGF-BB in the Platelet dry powder solution/suspension (PDPS) dilutions before nebulization (ng/mL) (Initial volume is 3 mL) | Volume of recovered solution after nebulization (mL) | PDGF-BB concentration in recovered solution after nebulization (ng/mL) |
|---|---|---|---|
| 1 | 1.1 | 2.8 | 1.2 |
| 2 | 2.8 | 2.75 | 2.9 |
| 3 | 5.2 | 2.7 | 5 |
| 4 | 12 | 2.7 | 11.3 |
| 5 | 22.4 | 2.65 | 16.1 |
| 6 | 29.2 | 2.6 | 20.1 |
| 7 | 56.2 | 2.2 | 46.5 |

TABLE 3

| The concentration of PDGF-BB in the Platelet dry powder solution/suspension (PDPS) dilutions before nebulization (ng/mL) | Calculation of PDGF-BB recovery after nebulization | percentage (%) |
|---|---|---|
| 1.1 | $(1.2 \times 2.8)/(1.1 \times 3) \times 100\% = 102\%$ | 102 |
| 2.8 | $(2.9 \times 2.75)/(2.8 \times 3) \times 100\% = 95\%$ | 95 |
| 5.2 | $(5 \times 2.7)/(5.2 \times 3) \times 100\% = 87\%$ | 87 |
| 12 | $(11.3 \times 2.7)/(12 \times 3) \times 100\% = 85\%$ | 85 |
| 22.4 | $(16.1 \times 2.65)/(22.4 \times 3) \times 100\% = 63\%$ | 63 |
| 29.2 | $(20.1 \times 2.6)/(29.2 \times 3) \times 100\% = 60\%$ | 60 |
| 56.2 | $(46.5 \times 2.2)/(56.2 \times 3) \times 100\% = 61\%$ | 61 |

Please refer to FIG. 1. FIG. 1 is a histogram showing the effect of PDGF-BB concentration of Platelet dry powder solution/suspension (PDPS) on the recovery of PDGF-BB after nebulization.

The results in FIG. 1 show that when the Platelet dry powder is mixed with normal saline to prepare the platelet dry powder solution/suspension (PDPS) dilutions with a PDGF-BB concentration less than or equal to 12 ng/mL, the recovery of PDGF-BB is as high as 85% or more (total PDGF-BB in recovered solution÷total amount of PDGF-BB in the Platelet dry powder solution/suspension (PDPS) dilutions×100%≥85%) after the steps of nebulization, collection of aerosols, and aggregation into recovered solution. On the other hand, if the Platelet dry powder is mixed with normal saline to prepare the Platelet dry powder solution/suspension (PDPS) dilutions with a PDGF-BB concentration greater than or equal to 22.4 ng/mL, the recovery of PDGF-BB is about 60% (total PDGF-BB in recovered solution÷total amount of PDGF-BB in the Platelet dry powder solution/suspension (PDPS) dilutions×100%≒60%) after the steps of nebulization, collection of aerosols, and aggregation into recovered solution.

From the above-mentioned embodiment, when the Platelet dry powder was formulated into a Platelet dry powder solution/suspension (PDPS) with a PDGF-BB concentration of less than 22.4 ng/mL, within the concentration range is nebulized by the aerosol generator, the recovery of PDGF-BB was as high as 63% or more.

Preferably, when the Platelet dry powder is formulated into a Platelet dry powder solution/suspension (PDPS) with a PDGF-BB concentration less than or equal to 12 ng/mL, the recovery of PDGF-BB in the concentration range of platelet dry powder solution/suspension (PDPS) is up to 85% after nebulization by the aerosol generator, which has an unexpected effect.

Embodiment 3: The Effect of Different Kinds of Platelet Solutions on the Recovery of PDGF-BB after Nebulization and the Time Required for Nebulization Two kinds of platelet solutions were used in this embodiment, namely (1) Platelet-Rich Plasma (PRP) and, (2) Platelet dry powder solution/suspension (PDPS) prepared by mixing platelet dry powder and normal saline according to the method described in Embodiment 1. The concentrations of PDGF-BB in Platelet dry powder solution/suspension (PDPS) and Platelet-Rich Plasma (PRP) were analyzed by enzyme-linked immunosorbent assay (ELISA). Then serially diluted with water for injection to prepare 6 groups of Platelet dry powder solution/suspension (PDPS) dilutions containing different concentrations of PDGF-BB and 6 groups of Platelet-rich plasma (PRP) dilutions containing different concentrations of PDGF-BB, the PDGF-BB concentrations in the dilutions were made 4.5, 5.5, 9, 10, 19.5, and 20.5 ng/mL, respectively.

3 mL of Platelet dry powder solution/suspension (PDPS) dilutions and Platelet-rich plasma (PRP) dilutions from each group were taken and nebulized separately with an aerosol generator (Pulmogine™ model, HCmed) to obtain multiple aerosols separately. The time required to nebulize 3 mL of solution was recorded separately, and the aerosol obtained after nebulization of each group of solution was collected in a centrifuge tube, and the aerosol could collect in the centrifuge tube to form a recovered solution. The volume of the recovered solution of each group was further analyzed, and then the concentration of PDGF-BB in the recovered solution of each group was analyzed by enzyme-linked immunosorbent assay (ELISA), and the recovery of PDGF-BB after nebulization was calculated. The experimental results regarding PDGF-BB recovery are shown in Table 4, Table 5 and FIG. 2A-4C.

TABLE 4

| Serial Number | PDGF-BB concentration in dilution before nebulization (ng/mL) (Initial volume is 3 mL) | PDGF-BB concentration in recovered solution after nebulization (ng/mL) | | Volume of recovered solution after nebulization (mL) | |
|---|---|---|---|---|---|
| | | PRP | PDPS | PRP | PDPS |
| 1 | 4.5 | 2.5 | 3.5 | 2.7 | 2.75 |
| 2 | 5.5 | 3.5 | 4.5 | 2.6 | 2.7 |
| 3 | 9 | 5 | 8 | 2.4 | 2.7 |
| 4 | 10 | 6 | 9 | 2.4 | 2.65 |
| 5 | 19.5 | 12 | 15 | 2 | 2.6 |
| 6 | 20.5 | 13 | 16 | 2 | 2.6 |

TABLE 5

| PDGF-BB concentration before nebulization (ng/mL, original volume is 3 mL) | Calculation of PDGF-BB recovery after nebulization | |
|---|---|---|
| | PRP | PDPS |
| 4.5 | $(2.7 \times 2.5)/(4.5 \times 3) \times 100\% = 50\%$ | $(2.75 \times 3.5)/(4.5 \times 3) \times 100\% = 71.3\%$ |
| 5.5 | $(2.6 \times 3.5)/(5.5 \times 3) \times 100\% = 55.2\%$ | $(2.7 \times 4.5)/(5.5 \times 3) \times 100\% = 73.6\%$ |
| 9 | $(2.4 \times 5)/(9 \times 3) \times 100\% = 44.4\%$ | $(2.7 \times 8)/(9 \times 3) \times 100\% = 80\%$ |
| 10 | $(2.4 \times 6)/(10 \times 3) \times 100\% = 48\%$ | $(2.65 \times 9)/(10 \times 3) \times 100\% = 79.5\%$ |
| 19.5 | $(2 \times 12)/(19.5 \times 3) \times 100\% = 41\%$ | $(2.6 \times 15)/(19.5 \times 3) \times 100\% = 66.7\%$ |
| 20.5 | $(2 \times 13)/(20.5 \times 3) \times 100\% = 42.3\%$ | $(2.6 \times 16)/(20.5 \times 3) \times 100\% = 67.6\%$ |

Figure 2B:
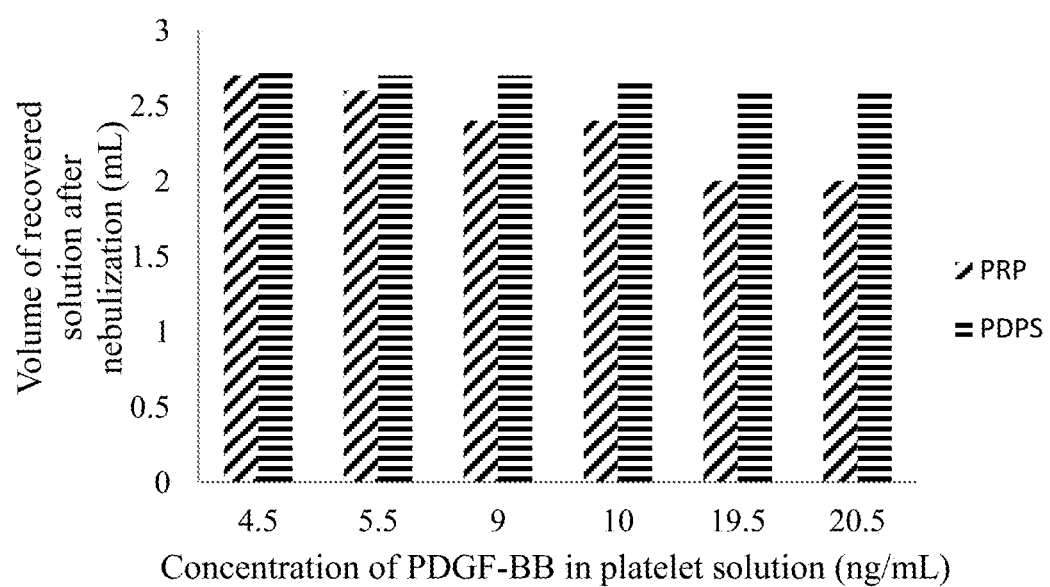
FIG. 2B: The histogram shows the effect of PDGF-BB concentration of different types of platelet solutions on the volume of the recovered solution after nebulization.
Figure 2C:
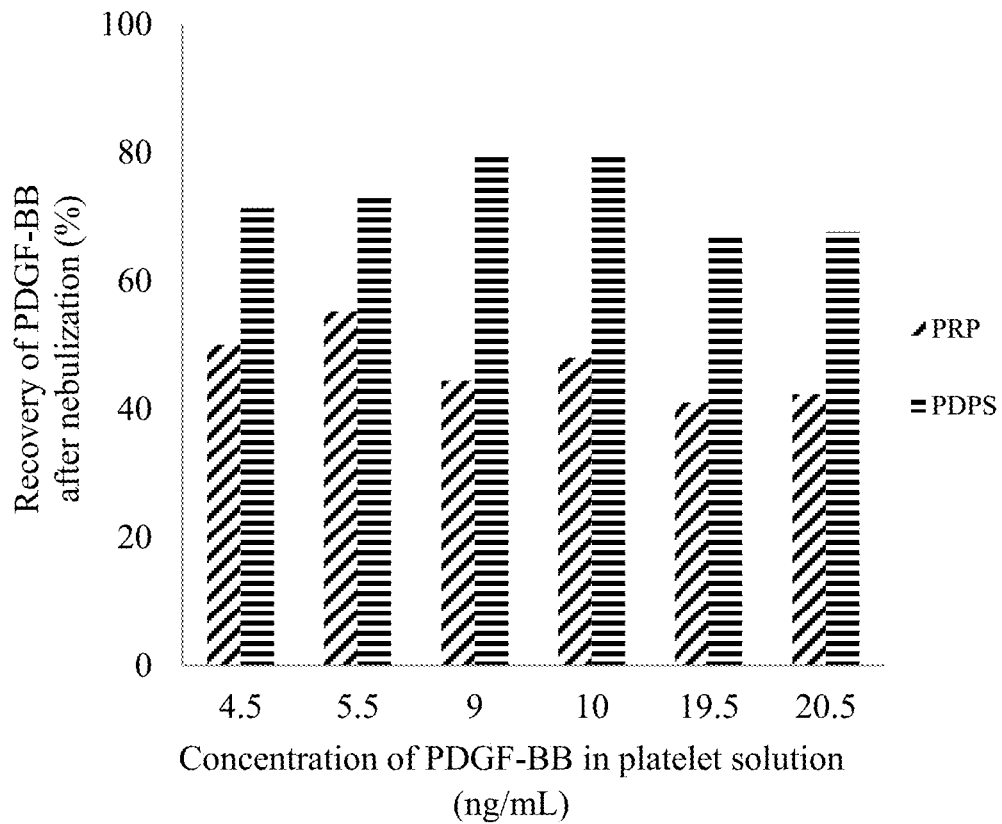
FIG. 2C: The histogram shows the effect of PDGF-BB concentration of different types of platelet solutions on the recovery of PDGF-BB after nebulization.

Please refer to FIG. 2A-2C. FIG. 2A is a histogram showing the effect of PDGF-BB concentration in different types of platelet solutions on the concentration of PDGF-BB in the recovered solution after nebulization; FIG. 2B is a histogram showing the effect of PDGF-BB concentration in different types of platelet solutions on the volume of the recovered solution after nebulization; FIG. 2C is a histogram showing the effect of PDGF-BB concentration in different types of platelet solutions on the recovery of PDGF-BB after nebulization.

As shown in FIG. 2C, comparing the nebulization results of two platelet solution dilutions containing the same PDGF-BB concentration [Platelet dry powder solution/suspension (PDPS) dilutions and Platelet-Rich Plasma (PRP) dilutions], the PDGF-BB recovery was higher for platelet dry powder solution/suspension (PDPS) dilutions than Platelet-rich plasma (PRP), with a difference of up to 35.6% (80%–44.4%=35.6%). What can be seen is that the Platelet dry powder solution/suspension (PDPS) prepared by the present invention can significantly improve the recovery of PDGF-BB after nebulization which has an unexpected effect compared to Platelet-Rich Plasma (PRP).

Figure 3:
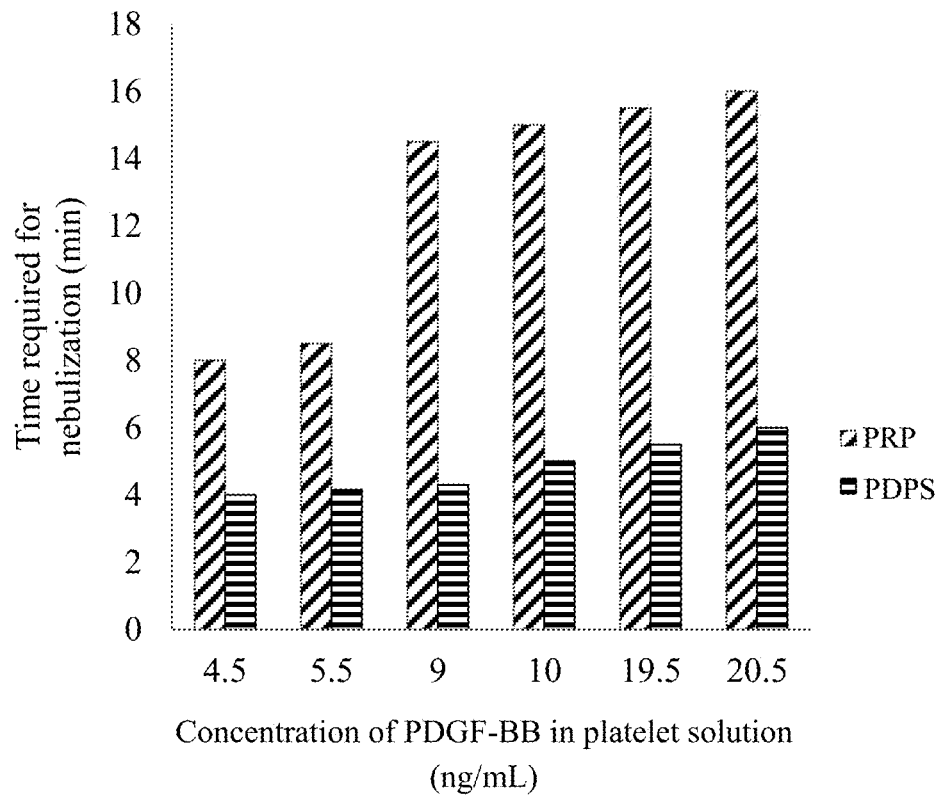
FIG. 3: The histogram shows the effect of PDGF-BB concentration of different types of platelet solutions on the time required for nebulization.

The experimental results regarding the time required for nebulization are shown in Table 6 and FIG. 3.

TABLE 6

| Serial Number | The concentration of PDGF-BB in different kinds of platelet solutions (ng/mL) (Initial volume is 3 mL) | Time required for nebulization (min) | |
|---|---|---|---|
| | | PRP | PDPS |
| 1 | 4.5 | 8 | 4 |
| 2 | 5.5 | 8.5 | 4.15 |

TABLE 6-continued

| Serial Number | The concentration of PDGF-BB in different kinds of platelet solutions (ng/mL) (Initial volume is 3 mL) | Time required for nebulization (min) PRP | PDPS |
|---|---|---|---|
| 3 | 9 | 14.5 | 4.30 |
| 4 | 10 | 15 | 5 |
| 5 | 19.5 | 15.5 | 5.5 |
| 6 | 20.5 | 16 | 6 |

Please refer FIG. 3. FIG. 3 is a histogram showing the effect of the PDGF-BB concentration on nebulization time for different types of platelet solutions.

As shown in FIG. 3, comparing the nebulization results of two platelet solution dilutions containing the same PDGF-BB concentration [Platelet dry powder solution/suspension (PDPS) dilutions and Platelet-Rich Plasma (PRP) dilutions], the nebulization time of Platelet dry powder solution/suspension (PDPS) dilutions is less than that of Platelet-rich plasma (PRP) dilutions, and the time required for nebulization can be reduced to at least half or even two-thirds. It can be seen that the Platelet dry powder solution/suspension (PDPS) prepared by the present invention can significantly reduce the time required for nebulization compared to Platelet-rich plasma (PRP), which has an unexpected effect.

Embodiment 4: the Effect of White Blood Cell (WBC) Concentration in Platelet Solution on Nebulization Embodiment 4-1: Effect of White Blood Cell (WBC) Concentration in Platelet Dry Powder Solution/Suspension (PDPS) on the Recovery of PDGF-BB after Nebulization and the Time Required for Nebulization Whole human blood is taken. Platelet dry powder was prepared from a portion of human whole blood using the method described in Embodiment 1; another portion of human whole blood was centrifuged and the aspirated in an aseptic manner with Buffy coat layer, with is the white blood cell concentrates.

Platelet dry powder was mixed with normal saline to obtain Platelet dry powder solution/suspension (PDPS).

Serial dilutions of white blood cell concentrates were performed with water for injection to prepare white blood cell concentrates with different white blood cell (WBC) concentrations of 10 dilutions.

Ten sets of platelet dry powder solution/suspension mixtures were prepared by mixing and diluting white blood cell concentrates of different white blood cell (WBC) concentrations with platelet dry powder solution/suspension (PDPS). 10 sets of platelet dry powder solution/suspension mixtures contained 0, 0.3, 0.5, 0.7, 1, 1. 7, 3, 5, 7 and $10 \times 10^3/\mu L$ (per microliter ($\mu L$) contained 0, 300, 500, 700, 1,000, 1,700, 3,000, 5,000, 7,000, and 10,000 white blood cells).

Among them, because of the thin thickness of the buffy coat layer, some platelets were inevitably aspirated at the same time during the preparation of the white blood cell concentrates. So, the PDGF-BB concentrations in the mixture of the 10 sets of Platelet dry powder solution/suspension were slightly different (about ±1.6 ng/mL). After further evaluation, the inventors found that these slight differences could be ignored.

3 mL of the solution was taken from each set of platelet dry powder solution/suspension mixture and multiple aerosols were obtained by nebulizing each set of Platelet dry powder solution/suspension (PDPS) mixture using an aerosol generator (Pulmogine™ model, HCmed). The time required to nebulize 3 mL of solution was recorded separately and centrifuge tubes were used to collect the aerosols obtained after nebulizing each set solutions separately. The aerosols were allowed to collect in the centrifuge tubes to form a recovered solution, and the volume of each set of recovered solutions was further analyzed. The concentration of PDGF-BB in each group of recovered solution was analyzed by enzyme-linked immunosorbent assay (ELISA), and then the recovery of PDGF-BB after nebulization was calculated. The experimental results regarding the recovery of PDGF-BB are shown in Table 7, Table 8 and FIG. 4A.

TABLE 7

| Serial Number | White blood cells (WBC) concentration in the platelet dry powder solution/suspension mixtures before nebulization ($\times 10^3/\mu L$) (Initial volume is 3 mL) | Volume of recovered solution after nebulization (mL) | PDGF-BB concentration in recovered solution after nebulization (ng/mL) |
|---|---|---|---|
| 1 | 0 | 2.4 | 2.5 |
| 2 | 0.3 | 2.4 | 2.5 |
| 3 | 0.5 | 2.2 | 2.7 |
| 4 | 0.7 | 2.2 | 2.6 |
| 5 | 1 | 2 | 2.6 |
| 6 | 1.7 | 1.8 | 3.5 |
| 7 | 3 | 1.6 | 3.6 |
| 8 | 5 | 1.5 | 4.3 |
| 9 | 7 | 1.2 | 4.5 |
| 10 | 10 | 1.1 | 5.4 |

TABLE 8

| White blood cells (WBC) concentration in the platelet dry powder solution/suspension mixtures before nebulization ($\times 10^3/\mu L$) (Initial volume is 3 mL) | Calculation of PDGF-BB recovery after nebulization | Percentage (%) |
|---|---|---|
| 0 | (2.5 × 2.4)/(2.8 × 3) × 100% = 71.4% | 71.4 |
| 0.3 | (2.5 × 2.4)/(2.9 × 3) × 100% = 69.0% | 69 |
| 0.5 | (2.2 × 2.7)/(3 × 3) × 100% = 66% | 66 |
| 0.7 | (2.2 × 2.6)/(2.6 × 3) × 100% = 73.3% | 73.3 |
| 1 | (2 × 2.6)/(3 × 3) × 100% = 57.8% | 57.8 |
| 1.7 | (1.8 × 3.5)/(3.9 × 3) × 10% = 53.9% | 53.9 |

TABLE 8-continued

| White blood cells (WBC) concentration in the platelet dry powder solution/suspension mixtures before nebulization (×10³/μL) (Initial volume is 3 mL) | Calculation of PDGF-BB recovery after nebulization | Percentage (%) |
|---|---|---|
| 3 | (1.6 × 3.6)/(4.5 × 3) × 100% = 42.7% | 42.7 |
| 5 | (1.5 × 4.3)/(4.5 × 3) × 100% = 47.8% | 47.8 |
| 7 | (1.2 × 4.5)/(4.1 × 3) × 100% = 43.9% | 43.9 |
| 10 | (1.1 × 5.4)/(5.3 × 3) × 100% = 37.4% | 37.4 |

Figure 4A:
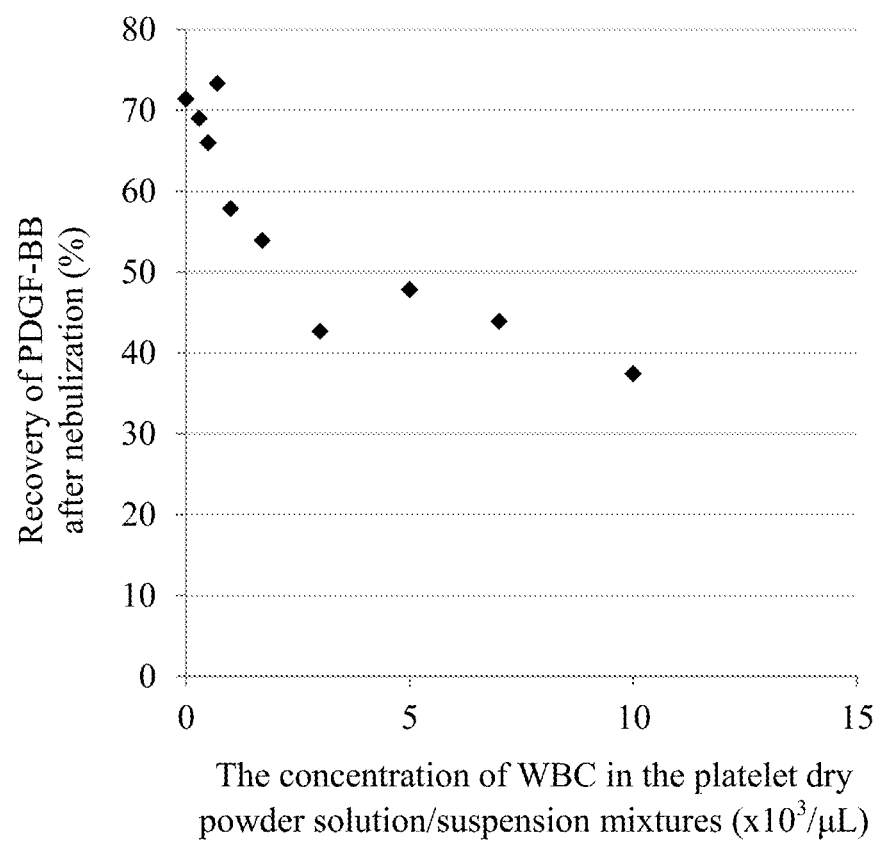
FIG. 4A: The scatter plot shows the effect of white blood cell (WBC) concentration in the Platelet dry powder solution/suspension (PDPS) on PDGF-BB recovery after nebulization.

Please refer to FIG. 4A. FIG. 4A is a scatter plot of the effect of the white blood cell (WBC) concentration in the platelet dry powder solution/suspension (PDPS) mixtures on PDGF-BB recovery after nebulization. The results in FIG. 4A show that when Platelet dry powder was formulated into a Platelet dry powder solution/suspension (PDPS) mixture with a white blood cell (WBC) concentration less than or equal to $1.7×10^3$ μL, after nebulization, aerosols collection and aggregation, the total recovery the solution, the content of PDGF-BB was as high as 53.9%. When the Platelet dry powder was formulated into a platelet dry powder solution/suspension (PDPS) with a white blood cell concentration less than or equal to $0.7×10^3/μL$, the recovery of the total PDGF-BB was as high as 66% or more.

From the above embodiments, when the Platelet dry powder was prepared into Platelet dry powder solution/suspension (PDPS) mixtures with the concentration of white blood cell (WBC) less than or equal to $1.7×10^3/μL$, the recovery of platelet dry powder solution/suspension (PDPS) mixtures in the above concentration range was over 53.9% after nebulization of Platelet dry powder solution/suspension (PDPS) by an aerosol generator which is an unexpected effect.

Preferably, the recovery of PDGF-BB was upwards of 66% when the platelet dry powder was formulated into a platelet dry powder solution/suspension mixture with a white blood cell (WBC) concentration less than or equal to $0.7×10^3/μL$, which had an unexpected effect when the platelet dry powder solution/suspension (PDPS) mixtures in this concentration range was nebulized by an aerosol generator.

Figure 4B:
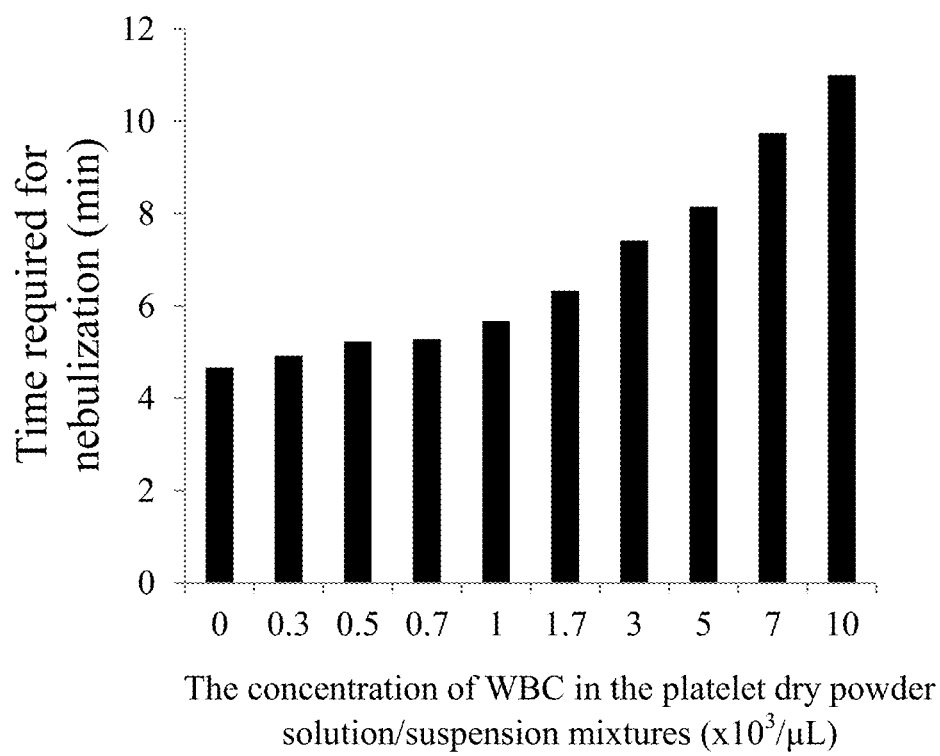
FIG. 4B: The histogram shows the effect of the white blood cell (WBC) concentration of the Platelet dry powder solution/suspension (PDPS) on the time required for nebulization.

The experimental results regarding to the time required for nebulization are shown in Table 9 and FIG. 4B.

TABLE 9

| Serial Number | Concentration of white blood cells (WBC) in the platelet dry powder solution/suspension mixtures before nebulization (ng/mL) | Time required for nebulization (min) |
|---|---|---|
| 1 | 0 | 4.67 |
| 2 | 0.3 | 4.92 |
| 3 | 0.5 | 5.23 |
| 4 | 0.7 | 5.28 |
| 5 | 1 | 5.67 |
| 6 | 1.7 | 6.33 |
| 7 | 3 | 7.42 |
| 8 | 5 | 8.15 |
| 9 | 7 | 9.75 |
| 10 | 10 | 11 |

Please refer to FIG. 4B. FIG. 4B is histogram showing the effect of the white blood cell (WBC) concentration of the platelet dry powder solution/suspension (PDPS) mixtures on the time required for nebulization.

As shown in FIG. 4B, when Platelet dry powder is formulated into Platelet dry powder solution/suspension mixtures with a white blood cell (WBC) concentration less than or equal to $1×10^3/μL$, the nebulization time required for nebulizing Platelet dry powder solution/suspension mixtures in these concentration range is short is similar (In FIG. 4B, when the white blood cell (WBC) concentration is less than or equal to $1×10^3/μL$, the slope of the graph is flat). When Platelet dry powder is formulated into Platelet dry powder solution/suspension mixtures and the concentration of white blood cell (WBC) is greater than $1×10^3/μL$, the nebulization time of Platelet dry powder solution/suspension mixtures increases significantly (in FIG. 4B, the slope of the graph starts to increase sharply when the concentration of white blood cell (WBC) is greater than $1×10^3/μL$). What can be seen is that the Platelet dry powder solution/suspension mixtures has an unexpected effect of significantly reducing the time required for nebulization when the concentration of white blood cells (WBC) is less than or equal to $1×10^3/μL$. The present inventors anticipate similar results when the experiments of this embodiment are performed with whole blood of mammals other than humans.

Embodiment 4-2: Detect the White Blood Cell
(WBC) Concentration in Platelet-Rich Plasma
(PRP) and the Recovery of PDGF-BB after
Nebulization Embodiment 4-1 Demonstrates the Reduced
Recovery of White Blood Cells (WBC) in
PDGF-BB in Platelet Dry Powder
Solution/Suspension Mixtures To confirm the concentration of white blood cells (WBC) in platelet-rich plasma (PRP) and the recovery of PDGF-BB after nebulization in the prior art, the following experiments were conducted by the present inventors.

In this experiment, platelet-rich plasma (PRP) specimens 1~3 were obtained using whole blood from 3 different individuals using the method of Example 1. Platelet-rich plasma (PRP) specimens 1~3 was analyzed for white blood cell (WBC) counts using an automated hematology analyzer (Model XP-300™, SYSMEX™ brand).

The experimental results showed that the concentration of white blood cells (WBC) in Platelet-rich plasma (PRP) specimens 1 to 3 was about $2×10^6$/mL.

The white blood cell (WBC) concentrates were mixed with the Platelet-rich plasma (PRP) vials 1~3 to produce the Platelet-rich plasma (PRP) mixtures 1~3 so that the white blood cell (WBC) concentration were all $4×10^3/μL$, and the PDGF-BB concentration were similar to the PDGF-BB concentration of the 10 mixtures of Embodiment 4-1, with a difference of about ±2.1 ng/mL. 3 mL of solution from the Platelet-rich plasma (PRP) mixture 1~3 was taken, separately, and an aerosol generator (Pulmogine™ model, HCmed) was used to nebulizer the solution of Platelet-rich plasma (PRP) mixture 1~3 to obtain a plurality of aerosols. The time required to nebulize 3 mL of the solution was recorded, and the aerosols were collected in centrifuge tubes, and the aerosols were collected in the centrifuge tubes to form a recovered solution. The PDGF-BB concentration in each recovered solution was analyzed by Enzyme-linked immunosorbent assay (ELISA), and the recovery of PDGF-BB after nebulization was calculated.

The experimental results showed that the recovery of PDGF-BB was 3.54%, 6.67% and 3.13% after the Platelet-rich plasma (PRP) mixtures 1~3 were nebulized in that order.

From comparing the results of Embodiment 4-1 and 4-2, it can be seen that even if the PDGF-BB concentration and the white blood cell (WBC) concentration are similar, such as a WBC concentration of 3~4×10³/μL, the difference in PDGF-BB concentration is only about ±2.1 ng/mL; the PDGF-BB recovery of the mixture prepared with platelet-rich plasma (3.13%~6.67%), still significantly lower than the PDGF-BB recovery (42.7%) prepared with the platelet dry powder solution/Suspension (PDPS) mixtures of the present invention, with a difference of up to 10-fold or more. What can be seen is that the platelet dry powder solution/suspension (PDPS) prepared with the platelet dry powder of the present invention can significantly improve the recovery of PDGF-BB after nebulization with unexpected effects compared with platelet rich plasma (PRP).

Embodiment 5: Particle Size and Proportion of Aerosols Prepared Using Platelet Dry Powder Entering Each Portion of the Respiratory Tract The human respiratory tract consists of various parts, which include the nasal cavity, nasal mucosa, trachea, bronchi, bronchioles, respiratory bronchioles, alveolar ducts and alveoli. The respiratory tract branches from the bronchi, and can branch at least 17 to 23 times from the respiratory bronchi to the alveoli; its purpose is to provide the body with the oxygen that it needs for gas exchange function.

This embodiment utilizes US and European certified the Next Generation impactor (NGI™) to analyze whether aerosols can enter the tissues of various portions of the respiratory tract after the nebulization of the present invention, and the distribution of aerosols in the tissues of various parts.

Figure 5A:
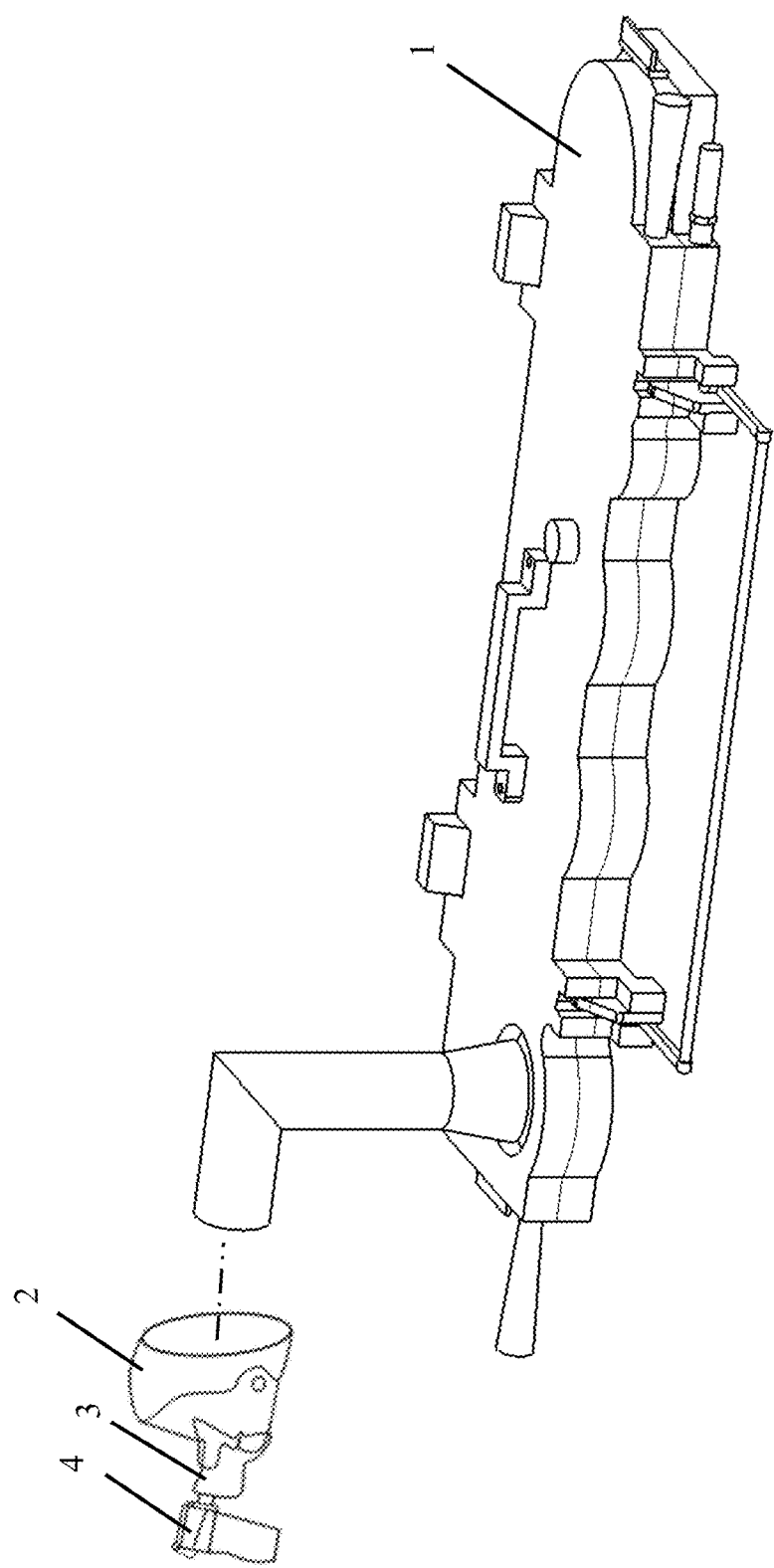
FIG. 5A: The diagram of closed state and use state of the Next Generation impactor.
Figure 5B:
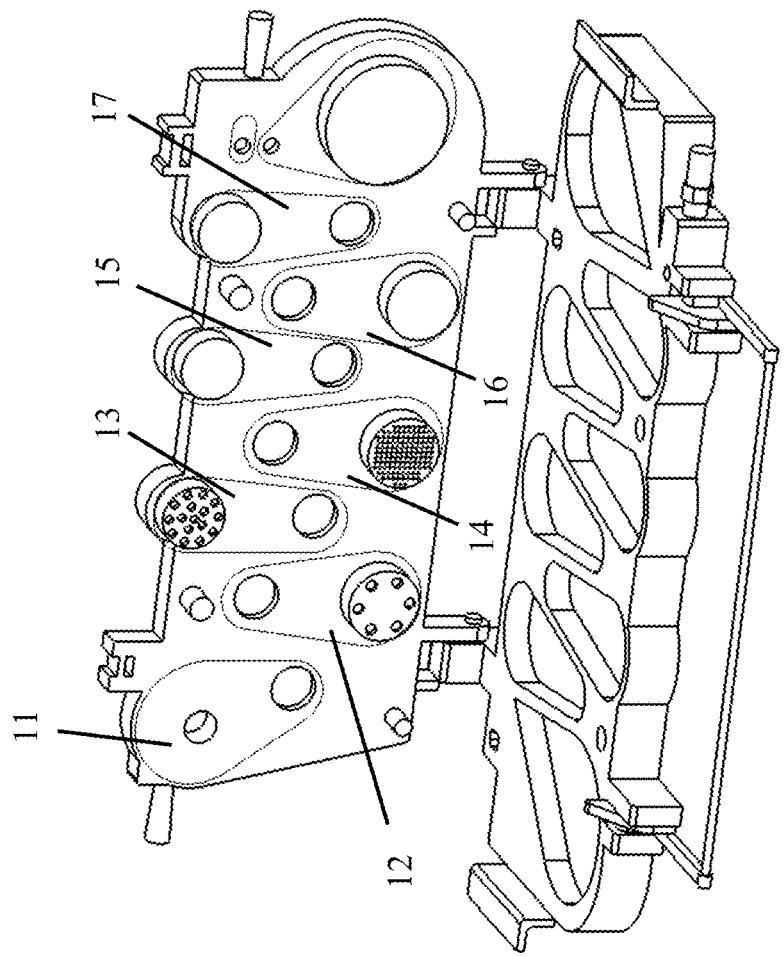
FIG. 5B: The diagram of open state of the Next Generation Impactor (includes various stages).

The Next Generation impactor (NGI™) simulates each part of the lung in seven stages from stage 1 to stage 7 and is designed according to the guidelines of the American Association for Respiratory Care. Please refer to FIG. 5A to FIG. 6. FIG. 5A is a schematic diagram of the closed state and use state of the Next Generation Impactor (NGI™); FIG. 5B is a schematic diagram of the open state of the Next Generation Impactor (NGI™) (including each stage). FIG. 6 shows the aperture size of each stage of the Next Generation Impactor (NGI™) and the simulated airway portion of each stage [the source of the data in FIGS. 5A~6 is the user manual of the Next Generation impactor (NGI™)], In FIG. 5A, the Next Generation Impactor (NGI™) 1 is connected to the simulated human head 2, and the nasal cavity of the simulated human head 2 is connected to the mask 3 and the nebulizer 4 in turn. in FIG. 5B, the Next Generation Impactor (NGI™) 1 includes a first stage 11, a second stage 12, a third stage 13, a fourth stage 14, a fifth stage 15, a sixth stage 16, and a seventh stage 17.

From FIG. 6, it can be seen that the first stage (stage 1) of the Next Generation Impactor (NGI™) simulates the nasal cavity and pharynx with an aperture size of 8.61~14.10 μm; the second stage (stage 2) simulates the trachea with an aperture size of 5.39~8.61 μm; the third stage (stage 3) simulates the bronchi with an aperture size of 3.3~5.39 μm; the fourth stage (stage 4) simulates bronchi or bronchioles with an aperture size of 2.08~3.30 μm; stage 5 (stage 5) simulates respiratory bronchioles with an aperture size of 1.36~2.08 μm; stage 6 (stage 6) simulates alveolar ducts with an aperture size of 0.98~1.36 μm; stage 7 (stage 7) simulates alveoli with an aperture size of <0.98 μm.

Platelet dry powder was mixed with normal saline to obtain Platelet dry powder solution/suspension (PDPS).

From the Platelet dry powder solution/suspension (PDPS), 3 mL of the solution was nebulized using an aerosol generator (model Pulmogine™, HCmed) under the conditions indicated in the United States Pharmacopoeia (USP) <1601>. After the Platelet dry powder solution/suspension (POPS) in the reservoir of the aerosol generator was emptied, the seven stage were washed with normal saline and to get recovered fluids of the seven states. The recovered fluid was dried in a freeze-drying machine (Lab 5 ST-3S, LSI) and then reconstitute by adding 1 milliliter (mL) water for injection of the 7 stages respectively. The concentration of PDGF-BB in each of the 7 stages was analyzed by ELISA, and the total amount and percentage of PDGF-BB in the multiple aerosols of the 7 stages (i.e., the total amount and percentage of PDGF-BB entering the anatomical location of the respiratory tract when applied to the human respiratory tract) was deduced. Please refer to Table 10 for the experimental results.

TABLE 10

| Serial number | NGI location | Aperture size range (μm) | The total amount of PDGF-BB entering the anatomical position of the respiratory tract (ng) | Percentage of PDGF-BB entering the anatomical position of the respiratory tract (%) |
|---|---|---|---|---|
| 1 | First stage (Stage 1) Nasal cavity, pharynx | 8.61~14.10 μm | 1.6 | (1.6/32.2) * 100 = 5% |
| 2 | Second stage (Stage 2) trachea | 5.39~8.61 μm | 6.8 | (6.8/32.2) * 100 = 21% |
| 3 | Third stage (Stage 3) bronchus | 3.3~5.39 μm | 7.8 | (7.8/32.2) * 100 = 24% |
| 4 | Forth stage (Stage 4) bronchiole | 2.08~3.30 μm | 9.9 | (9.9/32.2) * 100 = 31% |

TABLE 10-continued

| Serial number | NGI location | Aperture size range (μm) | The total amount of PDGF-BB entering the anatomical position of the respiratory tract (ng) | Percentage of PDGF-BB entering the anatomical position of the respiratory tract (%) |
|---|---|---|---|---|
| 5 | Fifth stage (Stage 5) respiratory bronchiole | 1.36~2.08 μm | 4.4 | (4.4/32.2)*100 = 14% |
| 6 | Sixth stage (Stage 6) alveolar duct | 0.98~1.36 μm | 0.9 | (0.9/32.2) * 100 = 3% |
| 7 | Seventh stage (Stage 7) alveoli | <0.98 μm | 0.8 | (0.8/32.2) * 100 = 2% |

As can be seen from Table 10, in this simulation experiment, the total PDGF-BB entering the nasal cavity and pharynx was 1.6 ng, and the PDGF-BB entering the nasal cavity and pharynx accounted for 5% (because the sum of PDGF-BB entering each tissue was 100%); the total PDGF-BB entering the trachea was 6.8 ng, and the PDGF-BB entering the trachea accounted for 21%; total PDGF-BB entering bronchus was 7.8 ng, and PDGF-BB entering bronchus accounted for 24%; total PDGF-BB entering bronchiole was 9.9 ng, and PDGF-BB entering bronchiole accounted for 31%; total PDGF-BB entering respiratory bronchiole was 4.4 ng, and PDGF-BB entering respiratory bronchiole accounted for 14%; the total amount of PDGF-BB entering the alveolar duct was 0.9 ng, and the PDGF-BB entering the alveolar duct accounted for 3%; the total amount of PDGF-BB entering the alveoli was 0.8 ng, and the PDGF-BB entering the alveoli accounted for 2%. What can be seen from this is that the aerosol and active ingredients (such as PDGF-BB) prepared by using platelet dry powder in the present invention can indeed enter various portions of the respiratory tract for the purpose of relieving inflammation or injury in various portions of the respiratory tract.

Embodiment 6: Effectiveness of Platelet Dry Powder Solution/Suspension (PDPS) Prepared from Platelet Dry Powder in Relieving Inflammation or Injury in Parts of the Respiratory Tract Lipopolysaccharide (LPS) is known to damage human lung fibroblasts (HFL1; ATCC® CCL-153™) and inhibit cell growth (see Refs, 6-8). In this embodiment, a model of lung cell inflammation was established using lipopolysaccharide (LPS; Sigma Aldrich® L2630) to assess the effect of platelet dry powder solution/suspension (PDPS) prepared from platelet dry powder on alleviating some of the inflammation or injury in the respiratory tract.

Human lung fibroblasts (HFL1; ATCC® CCL-153™) were cultured in Eagle's minimum essential medium (MEM, Sigma-Aldrich® M4655) containing 10% Fetal Bovine Serum (FBS). The culture was replaced with fresh culture medium for use. The human lung fibroblast HFL1 is described as an adherent cell.

The 96-well plate was divided into untreated wells, LPS control wells and multi-well experimental wells with 3 replicates each. This experiment was conducted in 2 batches, and the multiple experimental wells of the first batch included (1) PDGF-BB 1 ng/mL wells, (2) PDGF-BB 5 ng/mL wells, (3) PDGF-BB 10 ng/mL wells and (4) PDGF-BB 20 ng/mL wells; the multiple experimental wells of the second batch included (1) PDGF-BB 0.25 ng/mL wells, (2) PDGF-BB 0.5 ng/mL wells, (3) PDGF-BB 0.75 ng/mL wells, (4) PDGF-BB 1 ng/mL wells, (5) PDGF-BB 5 ng/mL wells, (6) PDGF-BB 7.5 ng/mL wells, (7) PDGF-BB 10 ng/mL wells, (8) PDGF-BB 12.5 ng/mL wells, (9) PDGF-BB 15 ng/mL wells and (10) PDGF-BB 17.5 ng/mL wells.

Human lung fibroblasts (HFL1) were added to the untreated wells, LPS control wells and experimental wells so that each well contained 7,000 cells and incubated for 48 hours at 37° C. in a 5% carbon dioxide (CO2) incubator.

Removal of old medium. The cells in LPS control wells and experimental wells were suspended in MEM culture medium (without FBS) containing 5 μg/mL LPS, and cells in untreated wells were suspended in MEM culture medium (without FBS) without LPS. The cells were incubated for 24 hours at 37° C. in a 5% carbon dioxide (CO2) incubator.

Removal of old medium. The cells in each well were suspended in MEM culture medium (without FBS) containing Platelet dry powder solution/suspension (PDPS), so that the concentration of PDGF-BB in several wells of the first experiment reached 1, 5, 10, and 20 ng/mL, respectively. The concentration of PDGF-BB in multiple wells of the second experiment reached 0.25, 0.5, 0.75, 1, 5, 7.5, 10, 12.5, 15, and 17.5 ng/mL, respectively. Cells in untreated wells and LPS control wells were suspended in MEM medium (without FBS) without Platelet dry powder solution/suspension (PDPS). The cells were incubated in an incubator at 37° C. with 5% carbon dioxide (CO2) for 24 hours.

Removal of old medium. Add 90 μl MEM and 10 μl CCK-8 buffer (Sigma-Aldrich®, product No. 96992) to each well. The wells were incubated for 4 hours at 37° C. in a 5% carbon dioxide ($CO_2$) incubator. Analysis was performed using a multi-function microplate spectrometer (SpectraMax® i3x model, MOLECULAR DEVICES™) with absorbance set at 450 nm. The regression curve between absorbance value and cell number was established according to the product description of CCK-8 buffer, and then the absorbance value was converted to the number of surviving cells.

Data were presented as mean±SD and statistically analyzed by T Test. Groups marked with "+" indicate statistical differences from untreated wells ($p<0.05$), while groups marked with "*" are statistically different from LPS control wells ($p<0.05$).

Please refer to FIG. 7A and FIG. 7B. FIG. 7A is a histogram showing the effect of Platelet dry powder solution/suspension (PDPS) (quantified as PDGF-BB concentration) on alleviating the inflammation and injury in human lung fibroblasts (the first batch of Embodiment 6); FIG. 7B is a histogram showing the effect of Platelet dry powder solution/suspension (PDPS) (quantified as PDGF-BB concentration) on alleviating inflammation and injury in human lung fibroblasts (the second batch of embodiment 6).

Figure 7A:
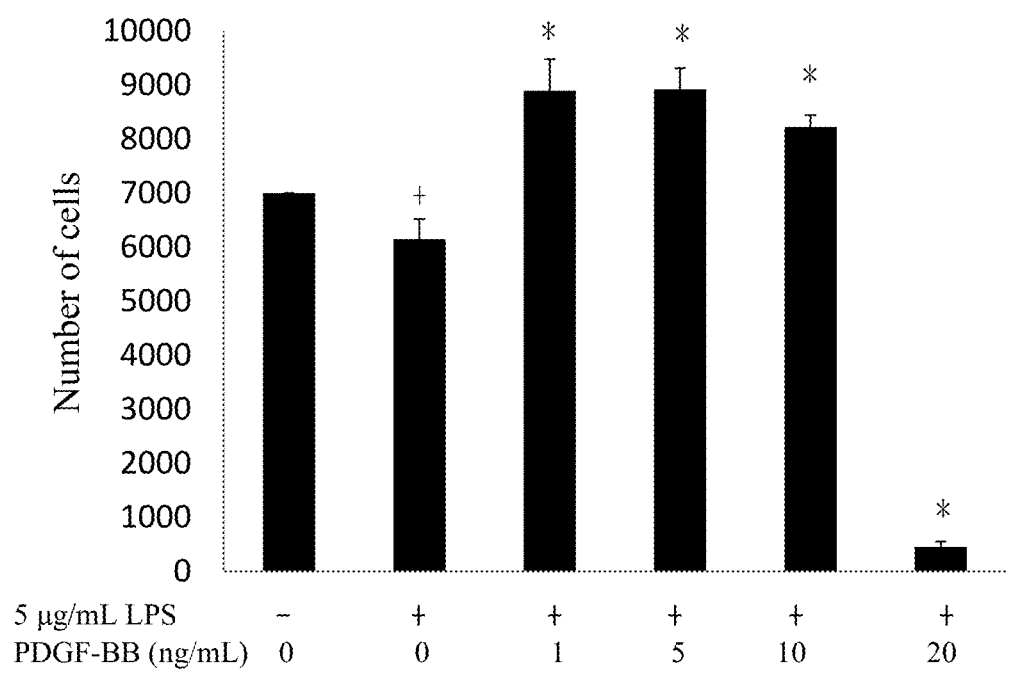
FIG. 7A: The histogram shows the effect of Platelet dry powder solution/suspension (PDPS) of the present invention (quantified as PDGF-BB concentration) on alleviating inflammation and injury in human lung fibroblasts (Embodiment 6, the first batch).
Figure 7B:
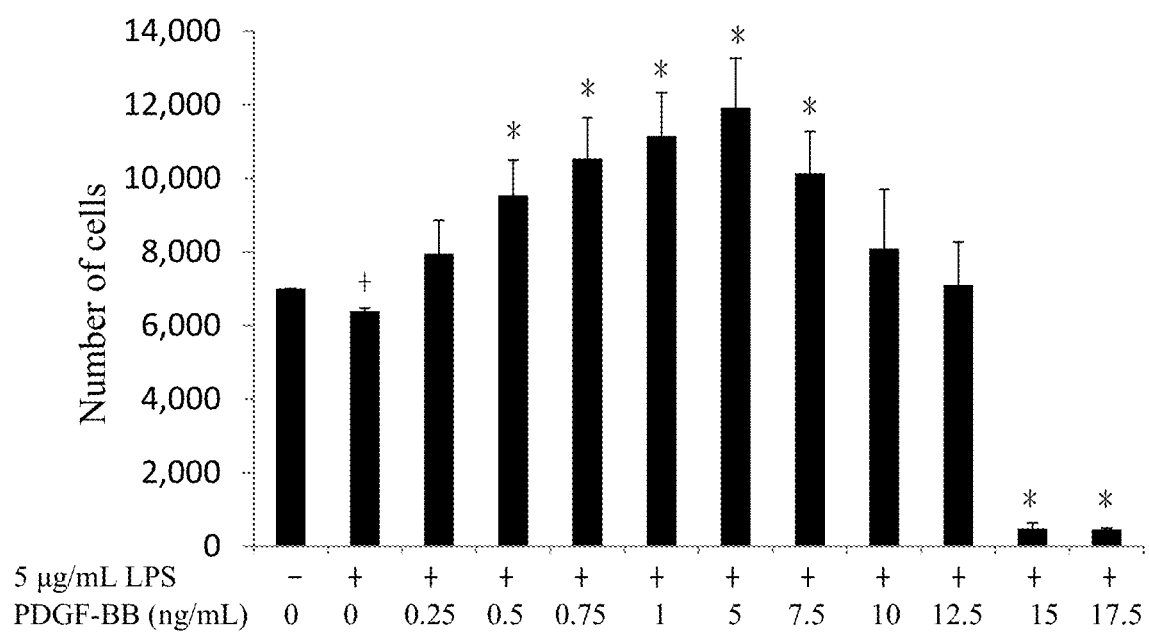
FIG. 7B: The histogram shows the effect of Platelet dry powder solution/suspension (PDPS) of the present invention (quantified by PDGF-BB concentration) on alleviating the inflammation and injury in human lung fibroblasts (Embodiment 6, the second batch).

What can be seen from FIG. 7A and FIG. 7B is that the Platelet dry powder solution/suspension (PDPS) in this case can effectively alleviate the inflammation or injury of lung cells caused by LPS and stimulate the growth of lung cells at appropriate doses.

Based on the similarity in inflammatory mechanisms between cells in other parts of the respiratory tract and human lung fibroblasts, the inventors anticipate that the platelet dry powder solution/suspension (PDPS) of the present invention will also be effective in alleviating inflammation or injury of cells in other parts of the respiratory tract by reducing the expression of inflammatory factors such as interleukin-6 (IL-6) and interleukin-8 (IL-8), thereby alleviating the degree of inflammation.

According to the results of this embodiment, it can be seen that the platelet dry powder solution/suspension (PDPS) prepared from the PDGF-BB-containing platelet dry powder in the present invention can alleviate or treat inflammation or injury of the respiratory tract.

The above description is only a preferred embodiments of the present invention and is not intended to limit the scope of the present invention. Therefore, all other changes or modifications shall be included within the scope of the patent application of the present invention without departing from the spirit of the invention as disclosed herein.

REFERENCES

| Serial number | References |
| --- | --- |
| 1 | Isable Andia, Nicola Maffulli, 2013. Platelet-rich plasma for managing pain and inflammation in osteoarthritis. Nature Review Rheumatology 15, 721-730. |
| 2 | Linfeng Piao, Hyungmin Park, and Chris Hyunchul Jo, 2017. Theoretical prediction and validation of cell recovery rates in preparing platelet-rich plasma through a centrifugation. PLOS ONE 12. |
| 3 | Sean R Downing, Giannoula L Klement, 2012. Isolation and proteomic analysis of platelets by SELDI-TOF MS. Methods in Molecular Biology 818: 153-170. |
| 4 | Zu-yao Chang, Gheorghe A. M. Pop and Gerard C. M. Meijer, 2004. A NOVEL MODEL OF BLOOD IMPEDANCE FOR INDIRECT VISCOSITY MEASUREMENT. |
| 5 | https://stanfordbloodcenter.org/buffy_coats/ |
| 6 | Cytokine 54 (2011) 289-295/Inhibited proliferation of human lung fibroblasts by LPS is through IL-6 and IL-8 release |
| 7 | Physiological Reports ISSN 2051-817X/CRISPLD2 (LGL1) inhibits proinflammatory mediators in human fetal, adult, and COPD lung fibroblasts and epithelial cells |
| 8 | Open Life Sciences 2021; 16: 108-127/Silencing XIST mitigated lipopolysaccharide (LPS)-induced inflammatory injury in human lung fibroblast WI-38 cells through modulating miR-30b-5p/CCL16 axis and TLR4/NF-κB signaling pathway |

What is claimed is:

1. A method of administering aerosols enriched in growth factors to a respiratory portion of a subject in need thereof, comprising:
   (A) mixing a platelet dry powder with a solvent to obtain a platelet dry powder solution/suspension, wherein a number of platelets per gram (g) of the platelet dry powder is $1\times10^6$ to $1\times10^{12}$ (1,000,000 to 1,000,000,000,000), and a number of white blood cells (WBC) per gram (g) of the platelet dry powder is 0-3,000;
   (B) nebulizing the platelet dry powder solution/suspension with an aerosol generator to obtain a plurality of aerosols; and
   (C) administering the aerosols to the respiratory portion of the subject in an amount that is effective in relieving or treating inflammation or injury of the respiratory portion of the subject.

2. The method according to claim 1, wherein the platelet dry powder is a freeze-dried powder.

3. The method according to claim 1, wherein the aerosols enter the subject through mouth or nose of the subject, thereby reaching the respiratory portion.

4. The method according to claim 1, wherein in step (A), the number of platelets per gram (g) of the platelet dry powder is $5\times10^9$ to $1\times10^{11}$ (5,000,000,000-100,000,000,000).

5. The method according to claim 1, wherein in step (A), a content of PDGF-BB per gram (g) of the platelet dry powder is 0.01-20,000 ng.

6. The method according to claim 5, wherein in step (A), a content of PDGF-BB per gram (g) of the platelet dry powder is 90-1,200 ng.

7. The method according to claim 1, wherein in step (A),
   a. a content of VEGF per gram (g) of the platelet dry powder is 200-200,000 pg; or
   b. a content of FGF per gram (g) of the platelet dry powder is 10-7,000 pg; or
   c. a content of TGF-β1 per gram (g) of the platelet dry powder is 200-10,000 ng; or
   d. a content of EGF per gram of the platelet dry powder is 0.5-500 ng.

8. The method according to claim 2, wherein the solvent is sterile normal saline, water for injection, 0.45% sodium chloride, 4.5% hypertonic saline, or isotonic saline.

9. The method according to claim 1, wherein in step (B), a number of platelets per milliliter (mL) of the platelet dry powder solution/suspension is $1\times10^8$ to $1\times10^{11}$ (100,000,000 to 100,000,000,000).

10. The method according to claim 1, wherein in step (B), a number of white blood cells (WBC) per milliliter (mL) of the platelet dry powder solution/suspension is 0 to $1\times10^6$ (0 to 1,000,000).

11. The method according to claim 1, wherein in step (B), a concentration of PDGF-BB in the platelet dry powder solution/suspension is 0.03-25 ng/mL.

12. The method according to claim 11, wherein in step (B), the concentration of PDGF-BB in the platelet dry powder solution/suspension is 0.25 to 12 ng/mL.

13. The method according to claim 1, wherein in step (B),
   a. a concentration of VEGF in the platelet dry powder solution/suspension is 10-4,000 pg/mL; or
   b. a concentration of FGF in the platelet dry powder solution/suspension is 1-200 pg/mL; or
   c. a concentration of TGF-β1 in the platelet dry powder solution/suspension is 5-250 ng/mL; or
   d. a concentration of EGF in the platelet dry powder solution/suspension is 0.1-10 ng/mL.

14. The method according to claim 1, wherein the aerosol generator is a non-invasive ventilation (NIV), nebulizer, ultrasonic nebulizer, small volume nebulizer (SVN), jet nebulizer, mesh nebulizer, vibrating mesh nebulizer, soft mist inhaler, or adaptive aerosol delivery (AAD).

15. The method according to claim 3, wherein the subject allows the aerosols to enter mouth or nose of the subject by maintaining spontaneous ventilation, mechanical air delivery, or pressure-controlled ventilation to reach the respiratory portion.

16. The method according to claim 1, wherein the aerosol generator can be attached to a mouthpiece or mask to deliver the aerosols to the respiratory portion of the subject through the mouth or nose of the subject.

17. The method according to claim 1, wherein the respiratory portion is nasal cavity, nasal mucosa, trachea, bronchi, bronchioles, respiratory bronchioles, alveolar ducts, alveoli or lungs.

18. The method according to claim 1, wherein the respiratory portion of the subject is inflamed, infected, or damaged.

19. The method according to claim 1, wherein the subject is a human; and
   the platelet dry powder is prepared from an autologous blood sample or an allogeneic blood sample.

* * * * *